(12) United States Patent
Ching

(10) Patent No.: US 8,809,519 B2
(45) Date of Patent: Aug. 19, 2014

(54) METHOD FOR NUCLEIC ACIDS ISOLATION

(75) Inventor: Jesus Ching, Saratoga, CA (US)

(73) Assignee: Luminex Corporation, Austin, TX (US)

( * ) Notice: Subject to any disclaimer, the term of this patent is extended or adjusted under 35 U.S.C. 154(b) by 964 days.

(21) Appl. No.: 12/747,802

(22) PCT Filed: Dec. 12, 2008

(86) PCT No.: PCT/US2008/086696
§ 371 (c)(1),
(2), (4) Date: Jan. 21, 2011

(87) PCT Pub. No.: WO2009/076645
PCT Pub. Date: Jun. 18, 2009

(65) Prior Publication Data
US 2011/0118457 A1    May 19, 2011

Related U.S. Application Data

(60) Provisional application No. 61/012,927, filed on Dec. 12, 2007.

(51) Int. Cl.
*C07H 21/00* (2006.01)
*C07C 315/00* (2006.01)
*C07C 317/00* (2006.01)

(52) U.S. Cl.
USPC .......................................... 536/25.4; 568/28

(58) Field of Classification Search
None
See application file for complete search history.

(56) References Cited

U.S. PATENT DOCUMENTS

| 4,696,980 A | 9/1987 | Porath |
| 7,964,380 B2 * | 6/2011 | Utermohlen et al. ......... 435/177 |
| 2006/0177855 A1 | 8/2006 | Utermohlen et al. |

OTHER PUBLICATIONS

Diogo et al., "Chromatography of pasmid DNA," J. Chromatography A 1069:3-22 (2005).
Lemmens et al., "Supercoiled plasmid DNA: selective purification by thiophilic/aromatic adsorption," J. Chromatography B 784:291-300 (2003).
Scoble and Scopes, "Ligand structure of the divinylsulfone-based T-gel," J. Chromatography A 787:47-54 (1997).
Young, "International Search Report," 3 pages, from International Patent Appl. No. PCT/US08/86696, United States Patent and Trademark Office, Alexandria, Virginia, USA (mailed Mar. 4, 2009).
Young, "Written Opinion of the International Searching Authority," 6 pages, from International Patent Appl. No. PCT/US08/86696, United States Patent and Trademark Office, Alexandria, Virginia, USA (mailed Mar. 4, 2009).
Hilz, et al., "Stimulation of proteinase K action by denaturing agents: application to the isolation of nucleic acids and the degradation of 'masked' proteins," *Eur. J. Biochem.*, 56:103-8, 1975.

\* cited by examiner

*Primary Examiner* — Lawrence E Crane
(74) *Attorney, Agent, or Firm* — Parker Highlander PLLC

(57) ABSTRACT

Methods for isolating nucleic acids using a solid phase having alkylene sulfonyl-containing compounds on its surface are provided. In one embodiment, the method comprises: contacting a sample containing nucleic acids with a solid phase having alkylene sulfonyl-containing compounds on its surface in a first aqueous solution to provide a loaded solid phase; washing the loaded solid phase with a second aqueous solution to provide a washed solid phase; and eluting the washed solid phase with a low ionic strength liquid to obtain the isolated nucleic acids. Kits containing a solid phase having alkylene sulfonyl-containing compounds also are provided.

33 Claims, 2 Drawing Sheets

METHOD FOR NUCLEIC ACIDS ISOLATION

CROSS-REFERENCE TO RELATED APPLICATION

This application is a U.S. National Stage of International Application number PCT/US2008/086696, filed Dec. 12, 2008, which claims benefit to U.S. Provisional Patent Application No. 61/012,927, filed on Dec. 12, 2007 and entitled "Method for Nucleic Acids Isolation", which is herein incorporated by reference in its entirety.

FIELD OF THE INVENTION

The present invention generally relates to methods of isolating nucleic acids.

BACKGROUND OF THE INVENTION

Given the importance of nucleic acids in biology, the isolation and purification of nucleic acids such as DNA and RNA is a fundamental step in molecular biology research. There is indeed a very large demand for nucleic acids analysis for various purposes. Moreover, samples for nucleic acids analysis are often taken from biological sources containing complex mixtures of biological molecules. Existing methods of obtaining high quality of nucleic acids are tedious, time-consuming, and costly. Thus, there is still a significant need in the art for additional nucleic acids isolation methods.

SUMMARY OF THE INVENTION

In one embodiment, the present invention provides a method for isolating nucleic acids comprising:

contacting a sample containing nucleic acids with a solid phase in a first aqueous solution having a pH from about 6 to about 9 to provide a loaded solid phase; wherein the first aqueous solution comprises one or more salts; and the surface of the solid phase comprises one or more functional groups having structural formula (I):

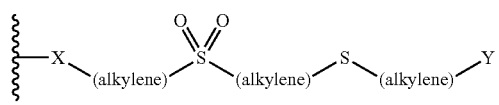

(I)

wherein,
X is $NR^1$, S, or O;
Y is —OH, —SH, —$NHR^2$, —$B(OH)_2$, or —$B(OR^3)_2$;
$R^1$ is hydrogen or alkyl;
$R^2$ is hydrogen, alkyl, or aryl; and
each $R^3$ is independently alkyl or aryl, or alternatively, two of $R^3$ together with the atoms to which they are bonded form a heterocyclyl;

washing the loaded solid phase with a second aqueous solution having a pH from about 6 to about 9 to provide a washed solid phase; wherein the second aqueous solution comprises a detergent and one or more salts; and eluting the washed solid phase with a low ionic strength liquid having a pH from about 5 to about 9 to obtain the isolated nucleic acids.

In another embodiment, the present invention provides a kit comprising:

a solid phase, wherein the surface of the solid phase comprises one or more functional groups having structural formula (I):

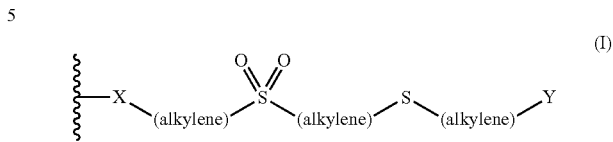

(I)

wherein,
X is $NR^1$, S, or O;
Y is —OH, —SH, —$NHR^2$, —$B(OH)_2$, or —$B(OR^3)_2$;
$R^1$ is hydrogen or alkyl;
$R^2$ is hydrogen, alkyl, or aryl; and
each $R^3$ is independently alkyl or aryl, or alternatively, two of $R^3$ together with the atoms to which they are bonded form a heterocyclyl;
one or more salts;
one or more buffering agents; and
an instruction document.

DETAILED DESCRIPTION OF THE INVENTION

Figure 1:
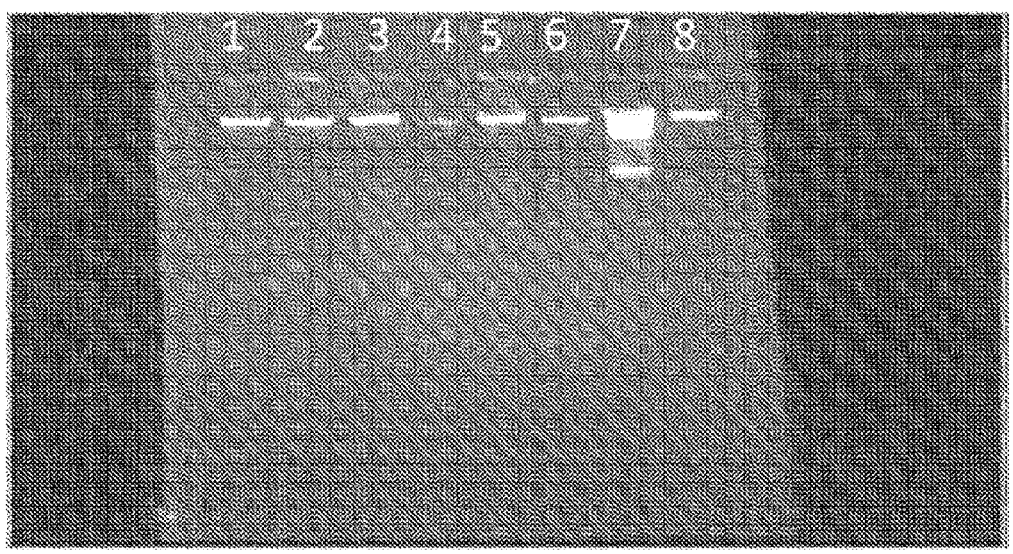
FIG. 1 shows agarose gel electrophoresis of DNA isolated from whole blood as described in Protocol A.

The present invention provides a method for isolating nucleic acids. In one embodiment, the present method comprises: contacting a sample containing nucleic acids with a solid phase in a first aqueous solution having a pH from about 6 to about 9 to provide a loaded solid phase; washing the loaded solid phase with a second aqueous solution having a pH from about 6 to about 9 to provide a washed solid phase; and eluting the washed solid phase with a low ionic strength liquid having a pH from about 5 to about 9 to obtain the isolated nucleic acids.

As used herein, the term "nucleic acids" denotes compounds containing two or more monomeric nucleotides in chain structure. The nucleic acids include natural nucleic acids, semi-natural nucleic acids, artificial nucleic acids, and combinations thereof. Examples of natural nucleic acids include, but are not limited to are deoxyribonucleic acid (DNA), ribonucleic acid (RNA), and fragments thereof. Semi-natural nucleic acids include compounds that are obtained from natural nucleic acids by chemically modifying natural nucleic acids and still contain two or more monomeric nucleotides in chain structure. Examples of artificial nucleic acids include, but are not limited to peptide nucleic acids (PNA), morpholino and locked nucleic acids (LNA), as well as glycol nucleic acids (GNA), and threose nucleic acids (TNA). Each of these artificial nucleic acids is distinguished from naturally-occurring nucleic acids by changes to the backbone of the molecule.

The method of the present invention can be used with any sample containing nucleic acids. The sample may originate from a biological or non-biological sources. Samples from biological sources include, but are not limited to biological tissues and fluids, such as, for example, plant or animal tissue, cells, bacteria, viruses, blood and blood plasma, sputum, saliva, sweat, tears, amniotic fluid, cerumen, mucus, semen, serum, urine, and etc. Samples from non-biological sources include, but are not limited to samples originated from a chemical reaction, air samples, and water (environmental sampling).

The sample can be processed by the present method with or without a pretreatment. By "pretreatment", it is meant treating the original sample chemically, physically, or biologically before the contacting step. The pretreatment can be dilution, filtration, solubilization, cell lysis, proteinase digestion, and etc. In one embodiment, the original sample is treated by a lysis process to release or liberate the nucleic acids, which may optionally be followed by protecting the liberated nucleic acids from nuclease activity. In another embodiment, the original sample is mixed with a solution for proteinase digestion wherein the solution contains a detergent, such as, Tween, sodium dodecyl sulfate, and urea; a buffering agent, such as, TRIS HCl; a chelating agent, such as EDTA; and one or more salts, such as, CaCl and MgCl. The proteinase digestion may be optimized by heating the solution to an appropriate temperature.

The solid phase of the present invention can be any solid material in various physical forms. Examples of the solid material include, but are not limited to celluloses, agaroses, glass, silica, papers, plastics, ceramics, porcelain, natural polymeric materials, synthetic polymeric materials, and combinations thereof. The solid materials can be in forms of particles, beads, microspheres, pellets, granules, spheroids, powder, sheets, slides, tubes, wells, probes, dipsticks, pipette tips, fibers, membranes, chips, biochips, and combinations thereof.

The surface of the solid phase comprises one or more functional groups having structural formula (I):

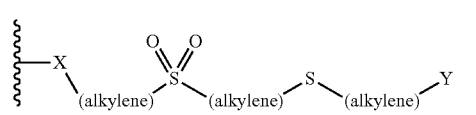

(I)

wherein,
X is $NR^1$, S, or O;
Y is —OH, —SH, —$NHR^2$, —$B(OH)_2$, or —$B(OR^3)_2$;
$R^1$ is hydrogen or alkyl;
$R^2$ is hydrogen, alkyl, or aryl; and
each $R^3$ is independently alkyl or aryl, or alternatively, two of $R^3$ together with the atoms to which they are bonded form a heterocyclyl.

In one embodiment of Formula (I), each alkylene is —$CH_2CH_2$—. In another embodiment of Formula (I), X is O and Y is —OH.

"Alkyl" is univalent hydrocarbon radical derived by the removal of one hydrogen atom from a single carbon atom of a parent saturated hydrocarbon. Alkyl may contain normal, secondary, tertiary or cyclic carbon atoms. An alkyl group typically has a formula of —$(C_nH_{2n+1})$, wherein n is an integer of 1 or greater. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl).

"Alkylene" is a divalent hydrocarbon radical derived by the removal of one hydrogen atom from a single carbon atom of a parent alkyl group. An alkylene group typically has a formula of —$(C_nH_{2n})$—, wherein n is an integer of 1 or greater. For example, an alkylene group can have 1 to 20 carbon atoms (i.e, $C_1$-$C_{20}$ alkylene), 1 to 10 carbon atoms (i.e., $C_1$-$C_{10}$ alkylene), or 1 to 6 carbon atoms (i.e., $C_1$-$C_6$ alkylene).

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Heterocyclyl" denotes a univalent radical formed by removing a hydrogen atom from a heterocyclic compound. "Heterocyclic compounds" are organic compounds containing at least one atom of carbon, and at least one element other than carbon, such as boron, sulfur, oxygen, or nitrogen within a ring structure.

The nucleic acids in the sample bind to the solid phase to form loaded solid phase when the sample is in contact with the solid phase in the first aqueous solution. The first aqueous solution comprises one or more salts. In one embodiment, the first aqueous solution has a pH from about 6 to about 9. In another embodiment, the first aqueous solution has a pH from about 6.5 to about 8.5. In another embodiment, the first aqueous solution has a pH from about 7 to about 8.

The contact step can be carried out in various way as long as the sample, the solid phase, and the first aqueous solution are mixed together and in physical contact for the nucleic acids in the sample to bind the solid phase through the functional group having structural formula (I). In one embodiment, the contact step comprises mixing the sample containing nucleic acids with the first aqueous solution to form a mixture; and adding the solid phase to the mixture. In another embodiment, the contact step comprises mixing the solid phase with the first aqueous solution to form a mixture; and adding the sample containing nucleic acids to the mixture. In another embodiment, the contact step comprises mixing the sample containing nucleic acids with the solid phase to form a mixture; and adding the first aqueous solution to the mixture. In another embodiment, the contact step comprises mixing the sample containing nucleic acids with the solid phase to form a mixture; and adjusting the condition of the mixture to obtain the first aqueous solution containing the solid phase and the sample containing nucleic acids, wherein the adjustment includes, among other things, adding water, one or more salt, and other optional ingredients to the mixture.

The unwanted material or substance is removed from the loaded solid phase to form a washed solid phase when the loaded solid phase is washed by the second aqueous solution. The washing step does not remove the nucleic acids from the loaded solid phase, thus the washed solid phase still has the nucleic acids attached thereon. The second aqueous solution comprises a detergent and one or more salts. In one embodiment, the second aqueous solution has a pH from about 6 to about 9. In another embodiment, the second aqueous solution has a pH from about 6.5 to about 8.5. In another embodiment, the second aqueous solution has a pH from about 7 to about 8.

In one embodiment of the present invention, the washing step comprises contacting the loaded solid phase with the second aqueous solution; and separating the loaded solid phase from the second aqueous solution to obtain the washed solid phase.

The one or more salts in the first and second aqueous solutions can be same or different. Suitable salts include chaotropic salts, kosmotropic salts, or combinations thereof. Depending on the sample to be used in the present method, the one or more salt can be present in various concentration. In one embodiment, the one or more salts are present in a concentration from about 0.1 M to about 6 M. In another embodiment, the one or more salts are present in a concentration from about 0.15 M to about 5 M. In another embodiment, the one or more salts are present in a concentration from about 0.2 M to about 4 M. In another embodiment, the one or more salts are present in a concentration from about 0.3 M to about 2 M.

Many existing methods for isolating nucleic acids are limited to using chaotropic salts solutions to bind nucleic acids to solid surfaces, such as silicia or inorganic oxides. In contrast, the present method can use both chaotropic salts solutions and kosmotropic salt solutions to liberate or solubilize the nucleic acid of interest prior to capture, and thereby broaden the choice of the binding solutions. Furthermore, unlike certain existing DNA isolation methods which use a particular type of solid material to bind DNA, the solid surface of the present invention can be a wide range of solid materials as supports in various physical forms having a functional group of structural formula (I). In the presence of various buffered aqueous solutions, the functional group produces an affinity based binding with targeted nucleic acids. In addition, the present method applies a washing step which selectively removes unwanted material, not the affinity bound nucleic acids, before the eluting step. Therefore, the present method provides a cost-effective method to obtain high quality nucleic acids from a sample.

As used herein, "chaotropic salts" refer to salts that decrease structuring of water, and thereby disrupts the three dimensional structure in macromolecules such as proteins, DNA, or RNA and denatures them. Chaotropic salts interfere with stabilizing intra-molecular interactions mediated by non-covalent forces such as hydrogen bonds, van der Waals forces, and hydrophobic effects. For example, when a chaotropic salt is added to a solution, the ion-dipole interaction between the chaotropic ion and water molecules results in breakdown of the unique hydrogen-bonded water structure. Such changes in the bulk water structure weakens the hydrophobic interactions, as discussed in von Hippel, P. H., and Schleich, T. (1969) in Structure and Stability of Biological Macromolecules (Timasheff, S, N., and Fasman, G. D., eds.) pp. 417-574, Marcel Dekker, Inc., New York. Since the nucleoprotein complexes are mainly stabilized by hydrophobic interactions, these complexes can be destabilized and dissociated by simply breaking the water structure using a chaotropic salt.

Suitable chaotropic cations for use in the formation of chaotropic salts include, but are not limited to $Cs^+$, $K^+$, $Na^+$, guanidinium, alkyl ammonium, aryl ammonium, and etc. Suitable chaotropic anions for use in the formation of chaotropic salts include but are not limited to perchlorate, thiocyanate, trichloroacetate, nitrate, iodide, bromide, chloride, urea, and etc. In one embodiment, the chaotropic salts are salts containing an ion selected from the group consisting of $SCN^-$, $H_2PO_4^-$, $HSO_4^-$, $HCO_3^-$, $I^-$, $Cl^-$, $NO_3^-$, $NH_4^+$, $Cs^+$, $K^+$, guanidinium, alkyl ammonium, aryl ammonium, and a combination thereof. In another embodiment, the chaotropic salts are guanidinium chloride, guanidinium isocyanate, sodium chloride, or a combination thereof As used herein, "kosmotropic salts" refer to salts that increase the stability and structure of water-water interactions. Kosmotropic salts can cause water molecules to favorably interact, which also stabilizes intermolecular interactions in macromolecules. Suitable kosmotropic salts include, but are not limited to salts formed by combining ions of the Hofmeister series. Examples of kosmotropic salts include, but are not limited to salts containing an ion selected from the group consisting of $SO_4^{2-}$, $HPO_4^{2-}$, $Mg^{2+}$, $Ca^{2+}$, $Li^+$, $Na^+$, $H^+$, $OH^-$ and $HPO_4^{2-}$. In one embodiment, the kosmotropic salts are selected from the group consisting of KCl, $MgCl_2$, $MgSO_4$, $(NH_4)_2SO_4$, $NaH_2PO_4$, $Ca(Ac)_2$, $(NH_4)_2SO_4$, $Cs_2SO_4$, $K_2SO_4$, $Na_2SO_4$, $Li_2SO_4$, $(NH_4)_2HPO_4$, $CsH_2PO_4$, $K_2HPO_4$, $NaH_2PO_4$, $LiH_2PO_4$, $NH_4CO_2CH_3$, $CsCO_2CH_3$, $KCO_2CH_3$, $NaCO_2CH_3$, $NH_4Cl$, CsCl, KCl, NaCl, LiCl, $NH_4Br$, CsBr, KBr, NaBr, and LiBr. The kosmotropic salts also include alkyl ammonium salts and aryl ammonium salts, the examples of which include $N(CH_3)_4Cl$, $(N(CH_3)_4)_2SO_4$, $N(Ph)_4Cl$, and $(N(Ph)_4)_2SO_4$.

The first and second aqueous solutions may optionally contain one or more buffer agents. The buffer agents in the first and second aqueous solutions may be same or different. By "buffering agent", it is meant an agent that adjusts the pH of a solution to the extent that the agent can maintain the pH of the solution within a certain pH range. The buffering agents are typically weak acid or weak base. Examples of the buffering agents include, but are not limited to 3-{[tris(hydroxymethyl)methyl]amino}propanesulfonic acid (TAPS), N,N-bis(2-hydroxyethyl)glycine (Bicine), tris(hydroxymethyl)methylamine hydrochloride (TRIS HCl), N-tris(hydroxymethyl)methylglycine (Tricine), 4-2-hydroxyethyl-1-piperazineethanesulfonic acid (HEPES), 2-{[tris (hydroxymethyl)methyl]amino}ethanesulfonic acid (TES), 3-(N-morpholino)propanesulfonic acid (MOPS), piperazine-$N,N^1$-bis(2-ethanesulfonic acid) (PIPES), dimethylarsinic acid (Cacodylate), 2-(N-morpholino)ethanesulfonic acid (MES), a phosphate salt, and a combination thereof.

Depending on the sample to be used in the present method, the one or more buffering agent can be present in various concentration. In one embodiment, the one or more buffering agents are present in a concentration from about 1 mM to about 2 M. In another embodiment, the one or more buffering agents are present in a concentration from about 3 mM to about 1 M. In another embodiment, the one or more buffering agents are present in a concentration from about 5 mM to about 600 nM. In another embodiment, the one or more salts are present in a concentration from about 7 mM to about 400 nM. In another embodiment, the one or more salts are present in a concentration from about 10 mM to about 200 mM.

In one embodiment of the present invention, the first and second aqueous solutions further independently comprises an alcohol or a polyalcohol. The alcohol can be any organic compound having a hydroxyl group. Examples of the alcohol include methanol, ethanol, isopropanol, and etc. By "polyalcohol", it is meant an organic compound containing multiple hydroxyl groups, particularly the organic compounds having an alkyl backbone. Examples of polyalcohol include ethylene glycol, glycerin, polyethylene glycol (PEG), and etc.

The detergent in the second aqueous solution can a cationic surfactant, a anionic surfactant, a non-ionic surfactant, an amphoteric surfactant, or a combination thereof. Examples of cationic surfactants include the surfactants based on quaternary ammonium cations, such as, cetyl trimethylammonium bromide (CTAB), cetylpyridinium chloride (CPC), polyethoxylated tallow amine (POEA), benzalkonium chloride (BAC), and benzethonium chloride (BZT). Examples of anionic surfactants include the surfactants based on sulfate, sulfonate or carboxylate anions, such as, perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate, also known as sodium lauryl ether sulfate (SLES), alkyl benzene sulfonate, and fatty acid salts. Examples of nonionic surfactants include alkyl poly(ethylene oxide); alkylphenol poly(ethylene oxide); copolymers of poly(ethylene oxide) and polypropylene oxide), a.k.a. Poloxamers or Poloxamines; alkyl polyglucosides, e.g., octyl glucoside and decyl maltoside; fatty alcohols, e.g., cetyl alcohol and oleyl alcohol; cocamide MEA (monoethanolamine); cocamide DEA (diethanolamine); polysorbates, e.g. Tween 20, Tween 80, and dodecyl dimethylamine oxide. Examples of zwitterionic surfactants include dodecyl betaine, cocamidopropyl betaine, and coco ampho glycinate.

In one specific embodiment, the first aqueous solution has a pH from about 7 to about 8 and contains a salt selected from ammonium sulfate and alkyl or aryl ammonium salts; a buffering agent selected from Hepes, TRIS HCl, MOPS, and phosphate; and optionally an alcohol selected from ethanol and isopropyl. In another specific embodiment, the first aqueous solution has a pH from about 7 to about 8 and contains sodium chloride; a buffering agent selected from Hepes, TRIS HCl, MOPS, and phosphate; a polyalcohol selected from PEG and ethylene glycol; and optionally an alcohol selected from ethanol and isopropyl. In another specific embodiment, the first aqueous solution has a pH from about 7 to about 8 and contains a salt selected from ammonium sulfate and alkyl or aryl ammonium salts; a buffering agent selected from Hepes, TRIS HCl, MOPS, and phosphate; a polyalcohol selected from PEG and ethylene glycol; and optionally an alcohol selected from ethanol and isopropyl.

In one specific embodiment, the second aqueous solution has a pH from about 7 to about 8 and contains a salt selected from guanidine HCl, guanidine isocyanate, and sodium chloride; a detergent selected from Tween 20, Triton X-100, lauryl sulfate, sodium dodecyl sulfate; a buffering agent selected from Hepes, TRIS HCl, MOPS, and phosphate; and optionally an alcohol selected from ethanol and isopropyl. In another specific embodiment, the first aqueous solution has a pH from about 7 to about 8 and contains a salt selected from ammonium sulfate and alkyl or aryl ammonium salts; a detergent selected from Tween 20, Triton X-100, lauryl sulfate, sodium dodecyl sulfate; a buffering agent selected from Hepes, TRIS HCl, MOPS, and phosphate; a polyalcohol selected from PEG and ethylene glycol; and optionally an alcohol selected from ethanol and isopropyl. In another specific embodiment, the first aqueous solution has a pH from about 7 to about 8 and contains a polyalcohol selected from PEG and ethylene glycol; a salt selected from ammonium sulfate and alkyl or aryl ammonium salts; a detergent selected from Tween 20, Triton X-100, lauryl sulfate, sodium dodecyl sulfate; a buffering agent selected from Hepes, TRIS HCl, MOPS, and phosphate; a polyalcohol selected from PEG and ethylene glycol; and optionally an alcohol selected from ethanol and isopropyl.

Elution of the washed solid phase with a low ionic strength liquid separates the nucleic acids from the solid phase. The term "low ionic strength liquid" denotes water or an aqueous solution having an ionic concentration lower than about 10 mM. In one embodiment, the ionic concentration is lower than about 8 mM. In another embodiment, the ionic concentration is lower than about 6 mM. In another embodiment, the ionic concentration is lower than about 4 mM. In another embodiment, the ionic concentration is lower than about 2 mM. In one embodiment, the ionic concentration is lower than about 1 mM.

The low ionic strength liquid has a pH from about 6 to about 8 and optionally comprises a buffering agent as described above, such as, for example, TRIS HCl. The low ionic strength liquid may further comprise a chelating agent, such as, for example, ethylenediaminetetraacetic acid (EDTA).

The elution step may be carried out with the low ionic strength liquid at room temperature or above, but not exceeding about 100° C. By "room temperature", it is meant a temperature range from about 18° C. to about 28° C. with the range from about 20° C. to about 25° C. more preferred. In one embodiment, the elution step is carried out with the low ionic strength liquid at about 30° C. In one embodiment, the elution step is carried out with the low ionic strength liquid at about 40° C. In one embodiment, the elution step is carried out with the low ionic strength liquid at about 50° C.

In one embodiment, the eluting step comprises contacting the washed solid phase with water or the low ionic strength solution; and separating the washed solid phase from water or the low ionic strength solution to obtain the isolated nucleic acids.

In another embodiment, the present invention provides a kit comprising a solid phase, wherein the surface of the solid phase comprises one or more functional groups having structural formula (I); one or more salts; one or more buffering agents; and an instruction document. In still other embodiments, the kit further comprises one or more empty containers. In yet another embodiment, the kit further comprises purified water in a container. In another embodiment, the kit further comprises an alcohol or a polyalcohol. The kit would facilitate one skilled in the art to practice the present method.

In another embodiment, the present method and/or kit may be used in combination with the device disclosed in the International Application No. PCT/US2006/040835, filed on Oct. 18, 2006, published as WO2007/047814, and entitled "CASSETTE FOR SAMPLE PREPARATION", the content of which is incorporated by reference in its entirety for all purposes.

Protocol A
1. Added 200 μL of blood to a centrifuge tube.
2. Added 190 μL of Lysis Buffer and 80 μL of Proteinase K to the centrifuge tube.
   a. Proteinase K (15 mg/ml)
      5 mM Ca $Cl_2$
      10 mM TRIS HCl
      pH 7.0
   b. Lysis Buffer
      6M Guanidine Hydrochloride
      10% Tween-20
      10 mM TRIS HCl
      pH 7.0
3. Vortexed the centrifuge tube for 10 seconds and incubated the same at room temperature for 10 minutes.
4. Added 100 μL of beads (20% slurry) to the contents inside the centrifuge tube.
5. Added 375 μL of isopropyl alcohol to the centrifuge tube, vortexed the contents for 5 seconds and incubated the same at room temperature for 5 minutes.
6. Placed centrifuge tubes on a magnetic rack to draw the particles to one side.
7. Pipetted the supernatant out of the tube leaving the magnetic particles.
8. Added 400 μL of Wash Buffer 1 to the centrifuge tube with the magnetic particles, vortexed, and removed supernatant after using a magnetic rack to retain the particles.
   a. Wash Buffer 1
      1.65 M Guanidine Hydrochloride
      10 mM TRIS—HCl
      0.25% Triton-X-100
      0.05% Tween-20
      1 mM EDTA
      50% Isopropanol
      pH 7.0

9. Added 400 μL of Wash Buffer 2 to the centrifuge tube with the magnetic particles, vortexed, and removed supernatant after using a magnetic rack to retain the particles.
 a. Wash Buffer 2.
   0.25 M Sodium Chloride
   10 mM TRIS—HCl
   0.05% Tween-20
   pH 7.0
10. Added 200 μL of water to the centrifuge tube containing the magnetic particles and mixed well and incubated the same at 56° C. for 10 minutes.
11. Used a magnetic rack to retain the magnetic particles and removed the supernatant from the magnetic particle. The genomic DNA was removed and ran on an agarose gel.

The results are indicated in FIG. 1, wherein Lane 1: sample 1; Lane 2: sample 2; Lane 3: sample 3; Lane 4: sample 4; Lane 5: sample 5; Lane 6: sample 6; Lane 7: Lambda/Hind III Standard; and Lane 8: Lambda DNA Control.

Protocol B

A blood sample was processed to isolate nucleic acids therein according to the procedure described below using magnetic solid phase material with the synthetic batches of functional group having structural formula (I).
 1. Added 200 μL of blood to a centrifuge tube.
 2. Added 80 μL of Proteinase K to the centrifuge tube.
  a. Proteinase K (15 mg/ml)
   5 mM CaCl$_2$
   10 mM TRIS HCl
   edpH 7.0
 3. Vortexed the centrifuge tube for 10 seconds and incubated the same at room temperature for 10 minutes.
 4. Added 100 μL of beads to the contents inside the centrifuge tube.
  a. Beads (20% slurry)
   3 M Ammonium sulfate
   10 mM TRIS HCl
   pH 7.0
 5. Added 375 μL of isopropyl alcohol to the centrifuge tube, vortexed the contents for 5 seconds and incubated the same at room temperature for 5 minutes.
  a. Isopropyl alcohol can be substituted with other alcohols such as ethanol and propanol.
  b. The alcohol may be eliminated if the sample matrix is precipitating.
  c. The alcohol may be substituted with polyethylene glycol (1-10%).
 6. Placed centrifuge tubes on a magnetic rack to draw the particles to one side.
 7. Pipetted the supernatant out of the tube leaving the magnetic particles.
 8. Added 400 μL of Wash Buffer 1 to the centrifuge tube with the magnetic particles, vortexed, and removed supernatant after using a magnetic rack to retain the particles.
  a. Wash Buffer 1
   1 M Sodium chloride
   10 mM TRIS—HCl
   0.25% Triton-X-100
   0.05% Tween-20
   pH 7.0
 9. Added 400 μL of Wash Buffer 2 to the centrifuge tube with the magnetic particles, vortexed, and removed supernatant after using a magnetic rack to retain the particles.
  a. Wash Buffer 2
   0.25 M Sodium Chloride
   10 mM TRIS—HCl
   0.05% Tween-20
   pH 7.0
10. Added 200 μL of water to the centrifuge tube containing the magnetic particles and mixed well and incubated the same at 56° C. for 10 minutes.
11. Used a magnetic rack to retain the magnetic particles and remove the supernatant from the magnetic particle. The genomic DNA was removed and ran on an agarose gel.

Figure 2:
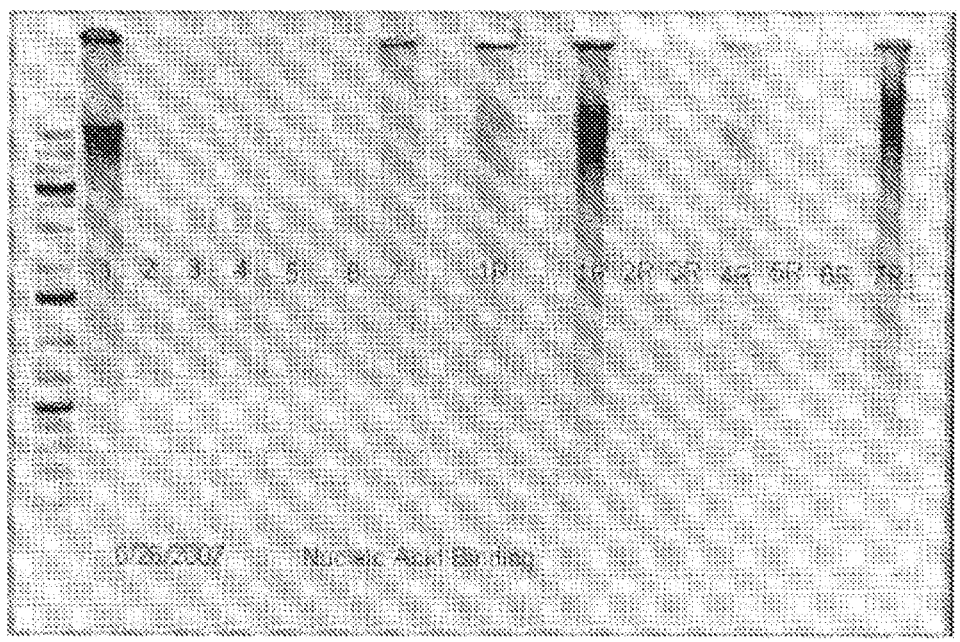
FIG. 2 shows agarose gel electrophoresis of DNA isolated from whole blood as described in Protocol B. Lanes 1 and 1 R: Positive Control; Lanes 2 to 7: Negative control; Lanes 2R to 7R: Various synthetic batches of the above Ligand on a solid phase material.

The results are indicated in FIG. 2, wherein Lanes 1 and 1R are positive controls; Lanes 2 to 7 are negative controls; and Lanes 2R to 7R are various synthetic batches of the functional group on a solid phase material. The synthetic batches 4R and 7R indicate nucleic acid binding.

All publications and patent applications herein are incorporated by reference to the same extent as if each individual publication or patent application was specifically and individually indicated to be incorporated by reference.

While the present invention has been particularly shown and described with respect to preferred embodiments thereof, it will be understood by those skilled in the art that the foregoing and other changes in forms and details may be made without departing from the spirit and scope of the invention. It is therefore intended that the present invention not be limited to the exact forms and details described and illustrated but fall within the scope of the appended claims.

I claim:

1. A method for isolating nucleic acids comprising:
 contacting a sample containing nucleic acids with a solid phase in a first aqueous solution having a pH from about 6 to about 9 to provide a loaded solid phase; wherein the first aqueous solution comprises one or more salts; and the surface of the solid phase comprises one or more functional groups having structural formula (I):

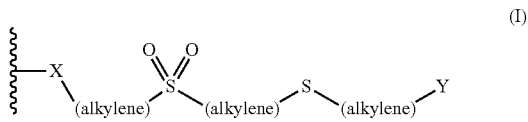

(I)

wherein,
 X is NR$^1$, S, or O;
 Y is —OH, —SH, —NHR$^2$, —B(OH)$_2$, or —B(OR$^3$)$_2$;
 R$^1$ is hydrogen or alkyl;
 R$^2$ is hydrogen, alkyl, or aryl;
 each R$^3$ is independently alkyl or aryl, or alternatively, two of R$^3$ together with the atoms to which they are bonded from a heterocyclyl; and ⸳ represents the point of attachment to the solid phase;
 washing the loaded solid phase with a second aqueous solution having a pH from about 6 to about 9 to provide a washed solid phase; wherein the second aqueous solution comprises a detergent and one or more salts; and
 isolating the nucleic acids by eluting the washed solid phase with a low ionic strength liquid having a pH from about 5 to about 9 to obtain the isolated nucleic acids.

2. The method of claim 1, wherein each alkylene is —CH$_2$CH$_2$—.

3. The method of claim 2, wherein X is O, and Y is —OH.

4. The method of claim 1, wherein the solid phase is in a form selected from the group consisting of particles, beads, microspheres, pellets, granules, spheroids, powder, sheets, chips, biochips, and combinations thereof.

5. The method of claim 1, wherein the one or more salts are chaotropic salts, kosmotropic salts, or combinations thereof.

6. The method of claim 5, wherein the chaotropic salts are salts containing an ion selected from the group consisting of $SCN^-$, $H_2PO_4^-$, $HSO_4^-$, $HCO_3^-$, $I^-$, $Cl^-$, $NO_3^-$, $NH_4^+$, $Cs^+$, $K^+$, guanidinium, alkyl ammonium, aryl ammonium, and a combination thereof.

7. The method of claim 5, wherein the chaotropic salts are guanidinium chloride, guanidinium isocyanate, or a combination thereof.

8. The method of claim 1, wherein eluting the washed solid phase comprises
contacting the washed solid phase with water or the low ionic strength solution; and
separating the washed solid phase from water or the low ionic strength solution to obtain the isolated nucleic acids.

9. The method of claim 5, wherein the kosmotropic salts are salts containing an ion selected from the group consisting of $SO_4^{2-}$, $HPO_4^{2-}$, $Mg^{2+}$, $Ca^{2+}$, $Li^+$, $Na^+$, $H^+$, $OH^-$ and $HPO_4^{2-}$.

10. The method of claim 5, wherein the kosmotropic salts are selected from the group consisting of KCl, $MgCl_2$, $MgSO_4$, $(NH_4)_2SO_4$, $NaH_2PO_4$, $Ca(Ac)_2$, $(NH_4)_2SO_4$, $Cs_2SO_4$, $K_2SO_4$, $Na_2SO_4$, $Li_2SO_4$, $(NH_4)_2HPO_4$, $CsH_2PO_4$, $K_2HPO_4$, $NaH_2PO_4$, $LiH_2PO_4$, $NH_4CO_2CH_3$, $CsCO_2CH_3$, $KCO_2CH_3$, $NaCO_2CH_3$, $NH_4Cl$, CsCl, KCl, NaCl, LiCl, $NH_4Br$, CsBr, KBr, NaBr, and LiBr.

11. The method of claim 1, wherein the first aqueous solution has a pH from about 7 to about 8.

12. The method of claim 1, wherein the second aqueous solution has a pH from about 7 to about 8.

13. The method of claim 1, wherein the low ionic strength liquid has a pH from about 6 to about 8.

14. The method of claim 1, wherein the low ionic strength liquid is at a temperature from about room temperature to about 100° C.

15. The method of claim 1, wherein the first and second aqueous solutions independently comprise one or more buffering agents.

16. The method of claim 1, wherein the low ionic strength liquid comprises a buffering agent.

17. The method of claim 15 or 16, wherein the one or more buffering agents are selected from the group consisting of 3-{[tris(hydroxymethyl)methyl]amino}propanesulfonic acid (TAPS), N,N-bis(2-hydroxyethyl)glycine (Bicine), tris (hydroxymethyl)methylamine hydrochloride (TRIS HCl), N-tris(hydroxymethyl)methylglycine (Tricine), 4-(2-hydroxyethyl)-1-piperazineethanesulfonic acid (HEPES), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), 2-(N-morpholino)ethanesulfonic acid (MES), a phosphate salt, and a combination thereof.

18. The method of claim 15 or 16, wherein the one or more buffering agents in the first and second aqueous solutions are independently present in a concentration from about 1 mM to about 2 M.

19. The method of claim 18, wherein the one or more buffering agents in the first and second aqueous solutions are independently present in a concentration from about 10 mM to about 200 mM.

20. The method of claim 1, wherein the first aqueous solution further comprises an alcohol or a polyalcohol.

21. The method of claim 1, wherein the second aqueous solution further comprises an alcohol or a polyalcohol.

22. The method of claim 20 or 21, wherein the alcohol is methanol, ethanol, or isopropanol.

23. The method of claim 20 or 21, wherein the polyalcohol is glycerol, ethylene glycol, or a liquid polyethylene glycol.

24. The method of claim 1, wherein the low ionic strength liquid further comprises a chelating agent.

25. The method of claim 1, wherein the detergent is a cationic surfactant, a anionic surfactant, a non-ionic surfactant, an amphoteric surfactant, or a combination thereof.

26. The method of claim 1, wherein the detergent is selected from the group consisting of lauryl sulfate, sodium dodecyl sulfate, polyethylene glycol p-(1,1,3,3-tetramethylbutyl)-phenyl ether (Triton X-100), and polysorbate 20.

27. The method of claim 1, wherein the one or more salts in the first and second aqueous solutions are independently present in a concentration from about 0.1 M to about 6 M.

28. The method of claim 1, wherein the one or more salts in the first and second aqueous solutions are independently present in a concentration from about 0.3 M to about 2 M.

29. The method of claim 1, wherein the contact step comprises
mixing the sample containing nucleic acids with the first aqueous solution to form it mixture, and
adding the solid phase to the mixture.

30. The method of claim 1, wherein the contact step comprises
mixing the solid phase with the first aqueous solution to form a mixture; and
adding the sample containing nucleic acids to the mixture.

31. The method of claim 1, wherein the contact step comprises
mixing the sample containing nucleic acids with the solid phase to form a mixture; and
adding the first aqueous solution to the mixture.

32. The method of claim 1, wherein the contacting step comprises
mixing the sample containing nucleic acids with the solid phase to form a mixture; and
adjusting the condition of the mixture to obtain the first aqueous solution containing the solid phase and the sample containing nucleic acids.

33. The method of claim 1, wherein the washing step comprises
contacting the loaded solid phase with the second aqueous solution; and
separating the loaded solid phase from the second aqueous solution to obtain the washed solid phase.

* * * * *

UNITED STATES PATENT AND TRADEMARK OFFICE
CERTIFICATE OF CORRECTION

PATENT NO. : 8,809,519 B2  Page 1 of 1
APPLICATION NO. : 12/747802
DATED : August 19, 2014
INVENTOR(S) : Jesus Ching It is certified that error appears in the above-identified patent and that said Letters Patent is hereby corrected as shown below:

In the Claims:

In claim 6, column 11, line 2, delete "$K^-$," and replace with --$K^+$,-- therefor.

In claim 29, column 12, line 30, delete "form it mixture" and replace with --form a mixture-- therefor.

Signed and Sealed this
Twenty-fifth Day of November, 2014

Michelle K. Lee
*Deputy Director of the United States Patent and Trademark Office*